United States Patent
Harding et al.

(10) Patent No.: US 8,719,068 B1
(45) Date of Patent: May 6, 2014

(54) INTELLIGENT SCHEDULING FROM MOBILE DEVICES

(75) Inventors: John A. Harding, Downey, CA (US); Jeffrey J. Guterman, Los Angeles, CA (US); George E. Mustafa, Los Angeles, CA (US)

(73) Assignee: 4 Patient Care, Downey, CA (US)

( * ) Notice: Subject to any disclaimer, the term of this patent is extended or adjusted under 35 U.S.C. 154(b) by 0 days.

(21) Appl. No.: 13/584,742

(22) Filed: Aug. 13, 2012

Related U.S. Application Data

(63) Continuation-in-part of application No. 12/813,498, filed on Jun. 10, 2010.

(60) Provisional application No. 61/523,343, filed on Aug. 13, 2011.

(51) Int. Cl.
*G06Q 10/00* (2012.01)
*G06Q 10/10* (2012.01)

(52) U.S. Cl.
CPC .................................. *G06Q 10/1095* (2013.01)
USPC .............................. 705/7.19; 705/7.18; 705/2

(58) Field of Classification Search
CPC ..... G06Q 50/22; G06Q 10/109; G06Q 10/10; G06Q 10/1095
USPC ................................................. 705/7.18, 7.19
See application file for complete search history.

(56) References Cited

U.S. PATENT DOCUMENTS

| | | | | |
|---|---|---|---|---|
| 7,584,253 | B2 * | 9/2009 | Curbow et al. | 709/206 |
| 7,937,422 | B1 * | 5/2011 | Ferguson, Jr. | 707/828 |
| 8,244,566 | B1 * | 8/2012 | Coley et al. | 705/7.11 |
| 2002/0116232 | A1 * | 8/2002 | Rapp et al. | 705/5 |
| 2010/0070296 | A1 * | 3/2010 | Massoumi et al. | 705/2 |
| 2010/0179916 | A1 * | 7/2010 | Johns et al. | 705/319 |
| 2010/0191566 | A1 * | 7/2010 | Loring et al. | 705/9 |
| 2011/0153380 | A1 * | 6/2011 | Velusamy | 705/7.19 |
| 2012/0209688 | A1 * | 8/2012 | Lamothe et al. | 705/14.27 |
| 2013/0032634 | A1 * | 2/2013 | McKirdy | 235/375 |
| 2013/0219479 | A1 * | 8/2013 | DeSoto et al. | 726/6 |

OTHER PUBLICATIONS

U.S. Appl. No. 61/523,343, filed Aug. 13, 2011; first named inventor: Harding.
U.S. Appl. No. 61/185,644, filed Jun. 10, 2010; first named inventor: Harding.
U.S. Appl. No. 12/813,498, filed Jun. 10, 2010; first named inventor: Harding.

* cited by examiner

*Primary Examiner* — Johnna Loftis
(74) *Attorney, Agent, or Firm* — Law Office of David Hong

(57) ABSTRACT

A system and method for scheduling or completing multiple types of healthcare interactions from a mobile computing device. The system identifies a customer or a target; communicates and notifies the target via some communication means (SMS, e-mail, mailed Post Card) to schedule an appointment. There is an association between the delivered message and the specific target (such as a weblink and a key), which allows the target to access the scheduling system without a separate login process. This system also allows the target to verify and update data about the target and to schedule an appointment.

11 Claims, 7 Drawing Sheets

Smart Phone

Please validate the following information:

Name: Steve Burke
Address: 8512 Eglise Avenue, Pico Rivera, CA 90212
Home Phone: (562) 861-1812
Cell Phone: (562) 754-6759
Email: steveburke23131@yahoo.com
Insurance Carrier: Vision Service Plan
Insurance ID: 3251315
Appointment Reason: Comprehensive Eye Exam Correct | Need to make changes

Figure 3

INTELLIGENT SCHEDULING FROM MOBILE DEVICES

This application claims the benefit of U.S. Provisional Patent Application 61/523,343, filed on Aug. 13, 2011, which is incorporated by reference. This application is also a continuation in part of U.S. patent application Ser. No. 12/813, 498, filed on Jun. 10, 2010, which is incorporated by reference.

FIELD OF THE INVENTION

The field of the present invention relates to scheduling systems and methods of selectively integrating scheduling information and data with mobile communication devices.

SUMMARY OF THE INVENTION

The following invention disclosure details a method for scheduling or completing multiple types of interactions from a mobile device, not limited to a Smart Phone or tablet type personal computer (PC).

The following description will focus on scheduling from a mobile device, however this capability is applicable to other applications and other fields, such as healthcare.

The System identifies a Target (in this description the Patient), which is due for an appointment, and the System communicates with Target via some means, including SMS/text messaging (Short Message Service), email, postal, etc. Within this communication means, the system notifies the Target that they are due to schedule an appointment. As part of the communication, an association between the delivered message and the specific Target is made via some method, such as a web-link (possibly a web-link or a link for a mobile device, such as a smart phone), or a Quick Response code (QR) on a postal notification. If the Target proceeds with scheduling an appointment and activates the link, the appropriate information associated with the Target can be retrieved to facilitate the scheduling of the appointment.

Problem to be solved: scheduling an appointment on a smart phone or other mobile computing device via an existing web scheduler requires that the person scheduling their appointment enter information to login to their account, which can be difficult on a smart phone or mobile device.

To facilitate the transaction, this invention associates the SMS with a special "link" or the email with a special link or the postcard with a QR code, so that this "link" creates a one-to-one relationship with the patient. As a result, the patient does not need to login (via a username/password or entering other identifying information); the target patient just needs to answer a simple question or questions to validate themselves.

Further, this system also allows the business to remove the validation questions if not wanted or needed.

BRIEF DESCRIPTION OF THE DRAWINGS

FIG. 3 shows a view from a Smart Phone or other mobile computing device for a validation of previously known information from the System.

DESCRIPTION OF PREFERRED EMBODIMENTS

The following invention disclosure details a method for scheduling or completing multiple types of healthcare interactions from a mobile computing device, including but not limited to a Smart Phone or tablet type PC (personal computer) or other computing device.

The following description will focus on scheduling from a mobile device; however, this capability is applicable to other fixed or mobile computing or communication applications.

The System identifies a Target (in this description the Patient or a customer) due for an appointment, and the System communicates with Target via some means, including SMS/text messaging (Short Message Service), email, postal mail, etc. System refers to a scheduling or an appointment system or database. Within this communication means, the system notifies the Target that they are due to schedule an appointment.

As part of the communication, an association between the delivered message and the specific Target is made via some method, such as a web link (possibly a weblink or a link for a mobile device, such as a smart phone), or a Quick Response code (QR) on a postal notification. This "link" allows the Target to access with the System without separately logging onto the System.

If the Target activates the link and proceeds with scheduling an appointment, the appropriate information associated with the Target can be retrieved to facilitate the scheduling of the appointment.

SMS Description

In one possible embodiment in a healthcare practice, the System identifies a customer or a patient that is clinically or administratively due for an appointment. For example, this trigger may be due to a calendar event or some related activity, such as a blood test, a surgical procedure or a required test, CAT scan or X-Ray.

Figure 1:
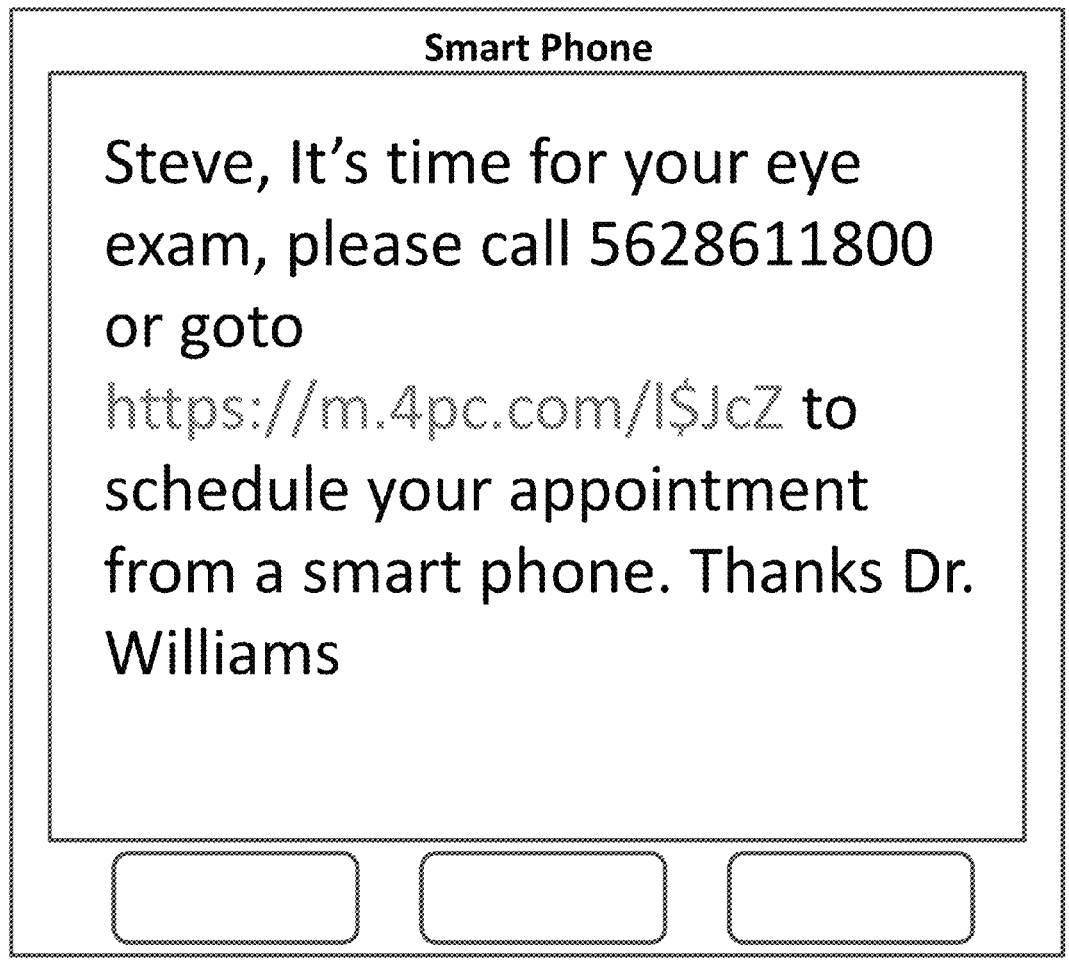
FIG. 1 shows a view from a Smart Phone or other mobile computing device for a sample SMS message.

The System creates a unique alert message for a patient, such as the following text message (an example is also illustrated in FIG. 1):

Steve, It's time for your eye exam, please call 5628611800 or goto https://m.4 pc.com/I$JcZ to schedule your appointment from a smart phone. Thanks Dr. Williams The link, which we will call the Patient Link in the above example is https://m.4 pc.com/$IJcZ, is personalized for a particular patient, and this Link has a one-to-one relationship to the patient Steve. The link consists of two components:

(1) a Website address (https://m.4 pc.com, which is the primary URL);
(2) the second component "$IJcZ" is a key, which creates a unique relationship between the business and the Target; in this case, the unique relationship between the healthcare provider at a specific practice and the target patient. This key is a first identifying code or another identifying marker.

Figure 2:
FIG. 2 shows a view from a Smart Phone or other mobile computing device for a sample Verification from the system.

If the Target activates the link, then one possible implementation is that the Target validates himself by optionally answering a question, such as providing his birthdate (an example is illustrated in FIG. 2).

The validation step is optional, and the decision to use such a validation step is determined by the business entity operating the System.

If the Target successfully validates their identity, then the System asks the Target to confirm that the information associated with the Target is accurate. If this information is not accurate, then the Target can update the information (a possible implementation is illustrated in FIG. 3).

Figure 4:
FIG. 4 shows a view from a Smart Phone or other mobile computing device for a selection of appointment.
Figure 5:
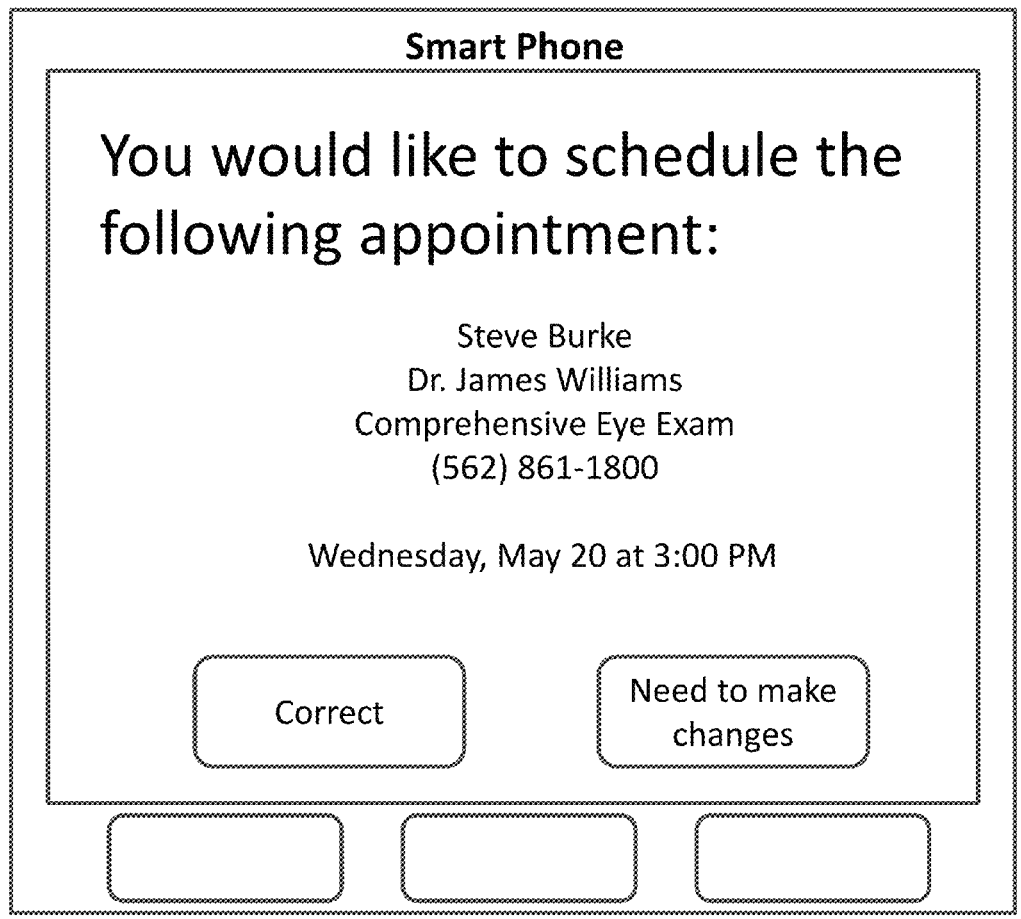
FIG. 5 shows a view from a Smart Phone or other mobile computing device for a confirmation of the appointment selection.
Figure 6:
FIG. 6 shows a view from a Smart Phone or other mobile computing device for a sample Intelligent Post Card integrated with a Smart Phone Scheduler.
Figure 7:
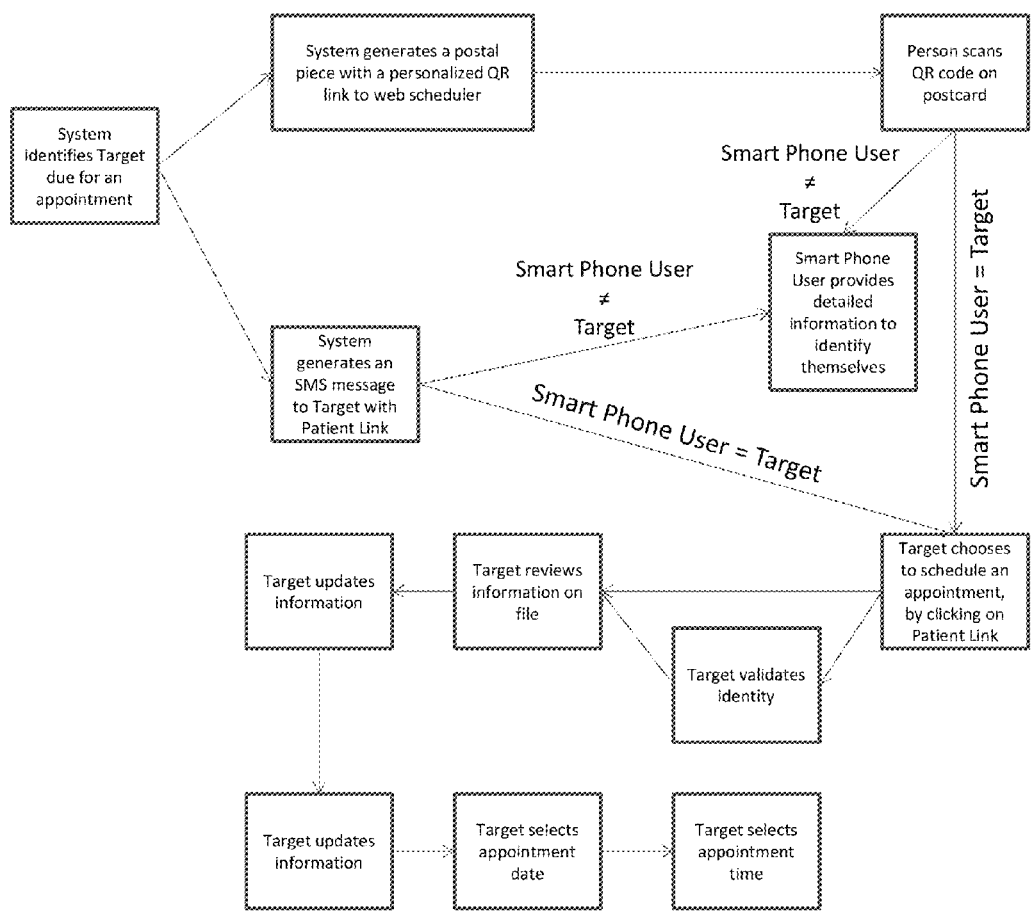
FIG. 7 shows a flowchart of the overall process for Intelligent Scheduling from a Mobile Communication or Computing Device.

The next step is for the System to allow the Target to schedule an appointment associated with the Target (as illustrated in FIGS. 4 and 5). If the Target did successfully complete the validation step prior to scheduling the appointment, then the appointment scheduled by the Target can be automatically written back into the business scheduling system, since there is a known one-to-one relationship with the Target and a record in the business scheduling system. If the Target had not validated themselves, then an additional step would be recommended for the association be made between the Target and an appropriate record in the business scheduling system. This additional step for un-validated records could include human intervention (via telephone, e-mail, text message, mail, etc.).

The scheduling system can be any data store that contains existing appointment information. When the Target schedules their appointment the System can limit the scheduling of appointments to slots that are available for scheduling the type of appointment desired by the Target. As a result, the System can follow the business rules of the business and prevent overbooking of appointments. An alternative approach would be for the invention to allow the Target to make an appointment request, instead of selecting a specific appointment date time.

If the user does not validate their identity, then the System requires that the user scheduling an appointment provide additional information to identify themselves. The information that a user may need to provide, if they do not successfully validate themselves, may include but not limited to:

Patient First Name
Patient Last Name
Patient Home Number
Patient Cell Number
Patient Work Number
Address 1
Address 2
City State
Zip
Birthdate Date
Gender
Insurance Carrier
Insurance ID
Appointment Type These requirements could be specified by the business entity as well. An alternative hybrid approach for a Target to entering this information, is for the System to ask the Target (using the System) from a mobile device if they would prefer to be called by the System to provide the required data via a phone call. If the Target prefers to provide the data verbally, then the System calls the Target on their mobile device (or a number provided by the Target) and records or captures the data provided through some means, such as Speech Recognition.

If Target properly validates himself, then the System can display the populated information, but the Target does not need to enter any of the information. If the Target determines that some of the information is outdated or incorrect, then the Target can choose to update the information.

Rescheduling from Smart Phone

An alternative utilization of the same technology is when a Target already has an appointment with a Business Entity. The Business Entity may send a SMS/Text Message reminder to the Target to assure that the Target remembers their appointment and comes to the appointment on time and properly prepared.

In another possible situation: a Target receives an appointment reminder via an SMS text message and chooses to cancel the appointment. For example, if the patient received the following message:

Steve, Please respond with a 1 if you will be able to keep your appt 6/3/11 at 11:00 am with Dr. Williams, 2 if you will not. Thank You.

If the Target chooses to cancel the appointment, then one possible implementation would result in a second message to the Target including the appropriate Patient Link so that that the Target could reschedule their appointment.

Steve, Please call 5628611800 to reschedule or https://m.4 pc.com/I$JcZ to reschedule your appointment from a smart phone. Thanks Dr. Williams Unscheduled Event Another alternative utilization of the same technology is when the Business Entity has an unexpected event and needs to cancel the existing appointments. A common example for this utilization would be a OB/GYN provider that needs to reschedule appointments when a delivery results in the current appointments being rescheduled. For example, Diane, Your 6/3/11 appt needs to be changed. Please call 5628611800 or https://m.4 pc.com/I$JcZ to reschedule your appt from a smart phone. Thx Williams OB/GYN Postal Description Another implementation of the technology is to incorporate the invention with postal communication. A Target due for an appointment is sent a postal communication, such as a postcard or letter. Within this postal communication a QR (Quick Response) code or equivalent is included with a personalized identification link, which connects this Target to a personalized URL for this Target.

If the Target scans the QR code and validates their identity, then they can run an application, which has been personalized for them, such as to schedule an appointment for the following reasons:

Appointment with Dr. James Williams
Comprehensive Eye Exam

Prior to completing the activity, the Customer or Target is allowed to make changes to the details of the application, which they are running. For example, if the patient would like to see a different doctor, other than Dr. James Williams.

This invention refers to computing programs, applications or software, which are all synonymous and are used interchangeably. This invention is preferably for mobile computing devices such as Mobile or Smart Phones, but this invention can be applied to any computing device that is connected to a communication network or the Internet via wire or wireless connection.

The embodiments of the invention may be implemented by a processor-based computer system. The system includes a database for receiving and storing information from users and application software for users, among other things, determining or updating usage, lifestyle characteristics, values and a user's profile, and displaying feedback information. In accordance with the present invention, computer system operates to execute the functionality for server component. Computer system includes a processor, a memory and a disk storage.

Memory stores computer program instructions and data. Processor executes the program instructions or software, and processes the data stored in memory. Disk storage stores data to be transferred to and from memory. Note that disk storage can be used to store data that is typically stored in the database.

All these elements are interconnected by one or more buses, which allow data to be intercommunicated between the elements. Note that memory is accessible by processor over a bus and includes an operating system, a program partition and a data partition. The program partition stores and allows execution by processor of program instructions that implement the functions of each respective system described herein. The data partition is accessible by processor and stores data used during the execution of program instructions.

For purposes of this application, memory and disk are machine readable mediums and could include any medium capable of storing instructions adapted to be executed by a processor. Some examples of such media include, but are not limited to, read-only memory (ROM), random-access memory (RAM), programmable ROM, erasable programmable ROM, electronically erasable programmable ROM, dynamic RAM, magnetic disk (e.g., floppy disk and hard drive), optical disk (e.g., CD-ROM), optical fiber, electrical signals, light wave signals, radio-frequency (RF) signals and any other device or signal that can store digital information. In one embodiment, the instructions are stored on the medium in a compressed and/or encrypted format.

As used herein, the phrase "adapted to be executed by a processor" is meant to encompass instructions stored in a compressed and/or encrypted format, as well as instructions that have to be compiled or installed by an installer before being executed by the processor. Further, system may contain various combinations of machine readable storage devices, which are accessible by processor and which are capable of storing a combination of computer program instructions and data.

A computer system also includes a network interface. A network interface may be any suitable means for controlling communication signals between network devices using a desired set of communications protocols, services and operating procedures. Communication protocols are layered, which is also referred to as a protocol stack, as represented by operating system, a CBE-communication layer, and a Transport Control Protocol/Internet Protocol (TCP/IP) layer.

Network interfaces may also include connectors for connecting interface with a suitable communications medium. Those skilled in the art will understand that network interfaces may receive communication signals over any suitable medium such as twisted-pair wire, co-axial cable, fiber optics, radio-frequencies, and so forth.

A typical computer system includes a processor, a memory, disk storage, a network interface, and a protocol stack having a CBE-communication layer and a TCP/IP layer. These elements operate in a manner similar to the corresponding elements for computer system.

A computer implemented method for a scheduling system for a service provider and a customer and a scheduling database and a communication system, comprising the following steps:
  a. the scheduling system identifies a customer for an appointment;
  b. the scheduling system transmits a message to the customer with a first identifying code and a website address link;
    (1) if the customer responds to the message with the first identifying code, then the system assigns the customer to the appointment;
    (2) if the customer does not successfully respond to the message with the first identifying code, then the system provides a question for the customer to provide a second identifying code;
  c. if the system recognizes the second identifying code of the customer, the system provides an existing information listing for the customer to review;
    (1) if the existing information is incorrect, the customer updates the existing information listing, and the system updates the existing information listing for the customer, and the system provides at least one appointment schedule date;
    (2) if the existing information is correct, the system provides at least one appointment schedule date;
    (3) if the customer selects the at least one appointment schedule date, the system provides at least one appointment time;
    (4) if the customer does not select the at least one appointment schedule date, the system provides at least one more appointment schedule date until the customer selects at least one appointment schedule date, and the system provides at least one appointment time;
  whereby once the customer selects at least one appointment schedule date and at least one appointment schedule time, the system updates the scheduling database.

The message is a Short Message Service (SMS), a text message, an electronic mail communication and a postal mail communication; the communication system is a Internet website, a wireless communication portal, a wired communication portal and the postal mailing system.

A computer implemented method for a scheduling system for a service provider and a customer and a scheduling database, comprising the following steps:
  a. the scheduling system identifies a customer for an appointment;
  b. the scheduling system transmits an electronic message to the customer with a first identifying code;
    (1) if the customer successfully responds to the electronic message with the first identifying code, then the system assigns the customer to the scheduling system;
    (2) if the customer does not successfully respond to the electronic message with the first identifying code, then the system provides a question for the customer to provide a second identifying code;
  c. if the system recognizes the first or the second identifying code of the customer, the system provides an existing information listing for the customer to review;
    (1) if the existing information is incorrect, the customer updates the existing information listing, and the system updates the existing information listing for the customer;
    (2) if the existing information is correct, the system provides at least one appointment schedule date;
    (3) if the customer selects the at least one appointment schedule date, the system provides at least one appointment time;
    (4) if the customer does not select the at least one appointment schedule date, the system provides at least one more appointment schedule date until the customer selects at least one appointment schedule date;
  whereby once the customer selects at least one appointment schedule date and at least one appointment schedule time, and the system updates the scheduling database.

A computer implemented method for a scheduling system for a service provider and a customer and a scheduling database, comprising the following steps:

a. the scheduling system identifies a customer for an appointment;

b. the scheduling system transmits a Short Message Service (SMS) text message to the customer with a key code and a website address link to the scheduling system;

c. the Short Message Service (SMS) text message has the key code create a specific link between the service provider and the customer;

d. If the customer activates the website address link, then the system asks the customer for at least one identifying piece of information;

e. If the customer successfully provides the at least one identifying piece of information, then the system displays the customer's current profile information;

f. the system asks the customer to confirm that the customer's current profile information is accurate;

g. if the customer's current profile information is not accurate, then the customer can update the customer's current profile information;

h. the customer can then select the appointment;

i. once the customer selects the appointment, the system updates the scheduling database with the customer and the key code, which has the specific link between the service provider and the customer; and j. if the appointment is not selected, the customer is given the option to contact the service provider via e-mail, Short Message Service (SMS) text message or telephone, whereby the customer has updated the customer's current profile information and selected the appointment, and whereby the scheduling database has been updated.

The customer can input the appointment time; the at least one identifying piece of information is a first name, a last name, a telephone number, mobile telephone number, an address, a city, a state, a zip code, a birth date, a gender, an insurance carrier name, an insurance identification number and an appointment type.

The system telephones the customer to initiate the scheduling system; when a customer already has an appointment with the system, the system sends a second message to remind the customer of the appointment; the customer can cancel or reschedule the appointment.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

Any section or paragraph headings are for the organization of the application and are not intended to be limiting.

Any element in a claim that does not explicitly state "means for" performing a specific function, or "step for" performing a specific function, is not be interpreted as a "means" or "step" clause as specified in 35 U.S.C. Sec. 112, Paragraph 6. In particular, the use of "step of" in the claims herein is not intended to invoke the provisions of 35 U.S.C. Sec. 112, Paragraph 6.

We claim:

1. A computer implemented method for a scheduling system for a service provider and a customer with a mobile communication device and a scheduling database and a communication system, comprising the following steps:

a. the scheduling system identifies a customer for an appointment;

b. the scheduling system transmits a message to the mobile communication device of the customer with a first identifying code and a website address link;

(1) if the customer responds to the message with the first identifying code and with the website address link, then the system assigns the customer to the appointment;

(2) if the customer does not successfully respond to the message with the first identifying code, then the system provides a question for the customer to provide a second identifying code;

c. if the system recognizes the second identifying code of the customer, the system provides an existing information listing for the customer to review;

(1) if the existing information is incorrect, the customer updates the existing information listing, and the system updates the existing information listing for the customer, and the system provides at least one appointment schedule date;

(2) if the existing information is correct, the system provides at least one appointment schedule date;

(3) if the customer selects the at least one appointment schedule date, the system provides at least one appointment time;

(4) if the customer does not select the at least one appointment schedule date, the system provides at least one more appointment schedule date until the customer selects at least one appointment schedule date, and the system provides at least one appointment time;

whereby once the customer selects at least one appointment schedule date and at least one appointment schedule time, the system updates the scheduling database.

2. The computer implemented method of claim 1 wherein the message is a Short Message Service (SMS), a text message and an electronic mail communication.

3. The computer implemented method of claim 1 wherein the communication system is an Internet website, a wireless communication portal and a wired communication portal.

4. A computer implemented method for a scheduling system for a service provider and a customer with a mobile communication device and a scheduling database, comprising the following steps:

a. the scheduling system identifies a customer for an appointment;

b. the scheduling system transmits an electronic message to the mobile communication device of the customer with a first identifying code and a specific website address link and a key between the service provider and the customer;

(1) if the customer successfully responds to the electronic message with the first identifying code and the specific website address link and the key between the service provider and the customer, then the system assigns the customer to the scheduling system;

(2) if the customer does not successfully respond to the electronic message with the first identifying code, then the system provides a question for the customer to provide a second identifying code;

c. if the system recognizes the first or the second identifying code of the customer, the system provides an existing information listing for the customer to review;

(1) if the existing information is incorrect, the customer updates the existing information listing, and the system updates the existing information listing for the customer;

(2) if the existing information is correct, the system provides at least one appointment schedule date;

(3) if the customer selects the at least one appointment schedule date, the system provides at least one appointment time;

(4) if the customer does not select the at least one appointment schedule date, the system provides at least one more appointment schedule date until the customer selects at least one appointment schedule date;

whereby once the customer selects at least one appointment schedule date and at least one appointment schedule time, and the system updates the scheduling database.

5. The computer implemented method of claim 4 wherein the message is a Short Message Service (SMS), a text message and an electronic mail communication.

6. A computer implemented method for a scheduling system for a service provider and a customer with a mobile communication device and a scheduling database, comprising the following steps:

a. the scheduling system identifies a customer for an appointment;

b. the scheduling system transmits a Short Message Service (SMS) text message to the mobile communication device of the customer with a key code and a website address link to the scheduling system;

c. the Short Message Service (SMS) text message has the key code create a specific link between the service provider and the customer;

d. If the customer activates the website address link, then the system asks the customer for at least one identifying piece of information;

e. If the customer successfully provides the at least one identifying piece of information, then the system displays the customer's current profile information;

f. the system asks the customer to confirm that the customer's current profile information is accurate;

g. if the customer's current profile information is not accurate, then the customer can update the customer's current profile information;

h. the customer can then select the appointment;

i. once the customer selects the appointment, the system updates the scheduling database with the customer and the key code, which has the specific link between the service provider and the customer; and j. if the appointment is not selected, the customer is given the option to contact the service provider via e-mail, Short Message Service (SMS) text message or telephone, whereby the customer has updated the customer's current profile information and selected the appointment, and whereby the scheduling database has been updated.

7. The computer implemented method of claim 6, wherein the customer can input the appointment time.

8. The computer implemented method of claim 6, wherein the at least one identifying piece of information is a first name, a last name, a telephone number, mobile telephone number, an address, a city, a state, a zip code, a birth date, a gender, an insurance carrier name, an insurance identification number and an appointment type.

9. The computer implemented method of claim 6 wherein the system telephones the customer to initiate the scheduling system.

10. The computer implemented method of claim 6 wherein when a customer already has an appointment with the system, the system sends a second message to remind the customer of the appointment.

11. The computer implemented method of claim 10 wherein the customer can cancel or reschedule the appointment.

* * * * *